United States Patent [19]

Minetola et al.

[11] Patent Number: 4,573,986
[45] Date of Patent: Mar. 4, 1986

[54] DISPOSABLE WASTE-CONTAINMENT GARMENT

[75] Inventors: James A. Minetola, Cincinnati; David R. Tucker, Mason, both of Ohio

[73] Assignee: The Procter & Gamble Company, Cincinnati, Ohio

[21] Appl. No.: 651,374

[22] Filed: Sep. 17, 1984

[51] Int. Cl.$^4$ .............................................. A61F 13/18
[52] U.S. Cl. .................................... 604/366; 604/365; 156/276; 156/291; 428/282
[58] Field of Search ....................... 604/365, 366, 384; 156/276, 291; 428/282, 171

[56] References Cited

U.S. PATENT DOCUMENTS

| | | | |
|---|---|---|---|
| 3,860,003 | 1/1975 | Buell | 604/385 |
| 3,913,579 | 10/1975 | Srinivasan et al. | 604/365 |
| 3,952,745 | 4/1976 | Duncan | 604/375 |
| 3,976,075 | 8/1976 | Chinai et al. | 604/365 |
| 3,978,257 | 8/1976 | Ring | 428/137 |
| 4,147,580 | 4/1979 | Buell | 156/291 |
| 4,269,188 | 5/1981 | Nishizawa et al. | 604/372 X |

Primary Examiner—William R. Dixon, Jr.
Assistant Examiner—Steven Capella
Attorney, Agent, or Firm—John M. Pollaro; Fredrick H. Braun; Richard C. Witte

[57] ABSTRACT

A disposable waste-containment garment such as a disposable diaper, an external incontinent protection garment for adults (e.g. adult incontinent briefs), an external catamenial, or a disposable liner for either a disposable diaper or an incontinent brief. The garment, which may be elasticized by, for example, having elasticized leg cuffs and waistbands, comprises an absorbent core comprising substantially unbonded fibers disposed between a liquid permeable lamina and a liquid impermeable backsheet, and the liquid permeable lamina and the absorbent core are bonded together in face to face relation with an open pattern of adhesive: preferably a fine scale reticulated network of filaments of pressure sensitive hot melt adhesive having a weight of from about one-half (½) milligram to about three (3) milligrams per square inch (from about 0.8 to about 4.7 grams per square meter) but, more preferably, from about one-and-three-tenths (1.3) milligrams to about two-and-three-tenths (2.3) milligrams per square inch (from about 2.0 to about 3.6 grams per square meter) and, most preferably, about two (2) milligrams per square inch (about 3.1 grams per square meter). In a preferred embodiment of such a garment, the liquid permeable lamina is a portion of a wet-strength-tissue envelope in which the absorbent core is disposed and secured; and the core further comprises elements of highly liquid absorbent matter which elements may be fibrous or particulate or the like in form. Additionally, such garments may further comprise additional laminae which may also be adhesively secured together or to the above enumerated elements: preferably in the manner in which the lamina described above is adhesively secured to the absorbent core.

32 Claims, 2 Drawing Figures

DISPOSABLE WASTE-CONTAINMENT GARMENT

DESCRIPTION

TECHNICAL FIELD

This invention relates to disposable waste-containment or collection garments, and pads and the like: in particular, disposable diapers, disposable external incontinent protection garments for adults which are broadly referred to as adult incontinent products such as briefs, liners for such diapers and briefs, and external catamenial pads. More specifically, this invention pertains to such garments which comprise absorbent cores comprising a mass of fibers substantially devoid of interfiber bonds (e.g. airlaid cores and airfelt cores and the like), and are laminated, and wherein particular laminae are adhesively secured together with particular patterns, quantities, and types of adhesives to achieve faster absorbency; less core slumping, cracking and roping; and increased tensile strength without substantially reducing either the softness or overall absorbency of such garments. The invention is particularly effective, for example, in elasticized laminated disposable diapers having elasticized leg cuffs and/or elasticized waistband regions inasmuch as unbonded laminae of such structures tend to blouse away from their respective absorbent cores even more than in non-elasticized disposable diapers, and thereby substantially impair effective urine absorption directly into their absorbent cores by a greater extent than in non-elasticized disposable diapers.

BACKGROUND ART

U.S. Pat. No. 4,147,580 which issued Apr. 3, 1979 to Kenneth B. Buell discloses a Method Of Bonding A Porous Fibrous Web To A Substrate: for example, a method of partially laminating a disposable diaper wherein hot melt adhesive globules are applied to the back surface of the diaper's topsheet by causing hot-melt adhesive to be wiped from a controlled thickness, contacting-type adhesive source. U.S. Pat. No. 3,978,257 which issued Aug. 31, 1976 to David F. Ring discloses an Internally Adhesively Bonded Fibrous Web: i.e., plural fibrous webs such as airlaid fibrous webs which are suitable for absorbent cores of disposable diapers are joined together in face to face relation so that the adhesive forms a scrim which is internal of the cores, and leaves the outwardly facing surfaces of the cores substantially free of adhesive. While these background patents have solved some of the problems relted to core/diaper integrity of laminated, disposable waste-containment garments and the like, they have not solved the problems to the extent nor in the manner of the present invention: particularly with respect to the blousing phenomenon described above although it is not intended to thereby limit the present invention.

DISCLOSURE OF THE INVENTION

In accordance with one aspect of the invention, a disposable waste-containment garment is provided which comprises an absorbent core of relatively unbonded fibers, a liquid permeable wet strength lamina, and a liquid impermeable backsheet. The absorbent core is disposed between the lamina and the backsheet, and the lamina is secured in face to face relation with the core by an open pattern of adhesive having an average weight of from about eight-tenths to about four-and-seven-tenths grams per square meter. In one more specific aspect of the invention the liquid permeable lamina is the topsheet of the garment (i.e., the element intended for contact with the user's skin), and in another aspect of the invention the liquid permeable lamina is disposed intermediate the topsheet of the garment and the absorbent core. In this aspect, the liquid permeable lamina may, for example, be wet strength tissue paper. In other aspects of the invention: the open pattern of adhesive may comprise a fine pattern of globulettes of adhesive or reticulated networks of filaments of adhesive which globulettes and filaments preferably have diameters about equal in order of magnitude to the effective average diameter of the fibers which constitute the absorbent core; the adhesive is hot melt adhesive; and/or the adhesive is pressure sensitive; and the quantity of adhesive may be limited to a smaller specific range or preferred value. Additional aspects of the invention may further comprise an additional laminae disposed between the absorbent core and the back sheet; the absorbent core may further comprise highly absorbent matter which is generically referred to and described hereinafter as supersorber material; the laminae may be associated to form an envelope which contains the absorbent core and obviates the core components from sifting out of the garment; and other open patterns of adhesive—preferably of the same type and level of adhesive as that constituting the open pattern of adhesive between the liquid permeable lamina and the absorbent core—may be incorporated in the garment intermediate other adjacent elements thereof.

BRIEF DESCRIPTIONS OF THE DRAWINGS

While the specification concludes with claims which particularly point out and distinctly claim the subject matter regarded as forming the present invention, it is believed the invention will be better understood from the following descriptions taken in conjunction with the accompanying drawings in which identical features in the several views are identically designated and in which:

DETAILED DESCRIPTION OF THE INVENTION

Figure 1:
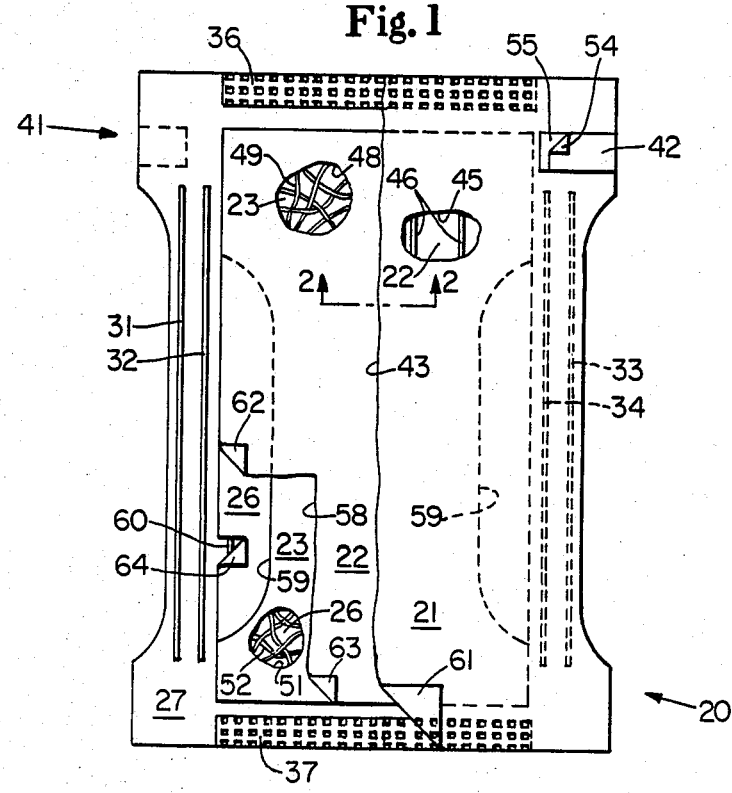
FIG. 1 is a plan view of an elasticized disposable diaper embodiment of the present invention in which view a number of portions are torn away and folded back to more clearly show the interior construction thereof.

Disposable diaper 20, FIG. 1, which is an exemplary embodiment of the present invention is shown to comprise a liquid permeable topsheet 21, a top wet-strength tissue 22, an absorbent core 23, a back wet-strength tissue 26, a liquid impermeable backsheet 27, elastic strands 31 through 34 which elasticize the leg cuff portions of the diaper, elastic bands 36 and 37 which elasticize the waistband regions of the diaper, and tape fasteners 41 and 42 (only a portion of fastener 41 being shown due to the left half of topsheet 21 having been torn away along line 43). For further clarity; a hole defined by edge 45 has been torn in the top sheet 21 to reveal a plurality of longitudinally extending hot melt glue beads 46 which secure the topsheet 21 to an underlying portion of top wet-strength tissue 22; a hole defined by edge 48 has been torn in top wet-strength tissue 22 to reveal an underlying portion of absorbent core 23 and a network 49 of filaments of a hot melt adhesive which is preferably pressure sensitive adhesive; a hole defined by edge 51 has been torn through the absorbent core 23 to show an underlying portion of the back wet-strength tissue 26 and a network 52 of filaments of hot melt adhesive which is also preferably pressure sensitive; a corner 54 of tape fastener 42 is folded back to reveal a portion of the underlying release tape 55 of the fastener assembly; a portion of the top wet-strength tissue 22 is torn away along line 58 to show underlying portions of the absorbent core 23, a notched side edge 59 of absorbent core 23, and underlying portions of the back wet-strength tissue 26, the backsheet 27, and a glue bead 60 which is one of a plurality of glue beads which adhere the backsheet 27 to the back wet-strength tissue 26; and corner 61 of topsheet 21, corners 62 and 63 of the top wet-strength tissue 22, and corner 64 of the back wet-strength tissue 26 are turned back to further elucidate the construction of diaper 20.

Figure 2:
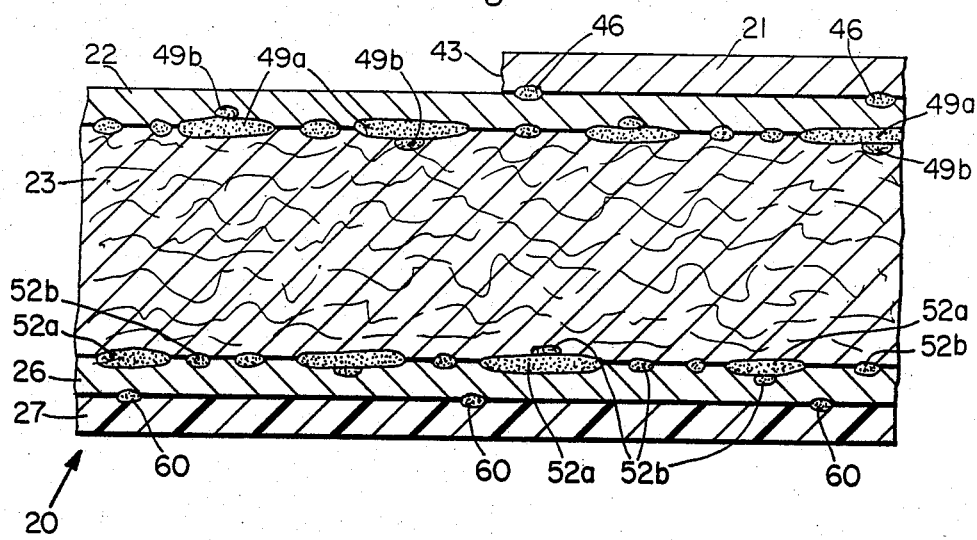
FIG. 2 is a fragmentary transverse sectional view taken along section line 2—2 of FIG. 1, and in which view the thickness of the laminae and the sizes of the adhesive formations are exaggerated for clarity.

In FIG. 2—a fragmentary sectional view of diaper 20, FIG. 1—the filament portions of the networks 49 and 52 of adhesive which are essentially longitudinally sectioned are designated 49a and 52a, respectively, and the filament portions which are essentially transversely sectioned are designated 49b and 52b, respectively. The abutting pairs of 49a/49b and 52a/52b depict inter-filament junctures in the networks of adhesive. The relative sizes of the adhesive filaments, the adhesive beads 46 and 60, and the thicknesses of the laminae are exaggerated for clarity of the invention but also depict an exaggerated degree of closeness of the interface between the top wet-strength tissue 22 and the absorbent core 23 when, preferably, that interface is eighty (80) percent or greater open area and, more preferably, at ninety (90). Additionally, FIG. 2 does not show the relative size relationship between the fibers which constitute absorbent core 23 and the filaments of the adhesive networks 49 and 52, FIG. 1. In fact, it is preferred that the adhesive filaments have diameters about equal in order of magnitude to the diameters of the fibers; and that the crossovers or junctures of the networks be substantially more closely spaced than the average length of the fibers of the core 23.

Basically, the low level of adhesive constituting the open pattern of adhesive 49 precipitates improved garment integrity in general, and more core integrity in particular without unduly negatively affecting absorbency or softness. More specifically, embodiments of the present invention have improved resistance to core cracking, slumping, and roping; and limited data indicate that reduced blousing as discussed above precipitates improved demand wetability as hereinafter defined and described. Of course, further improvement is realized in embodiments of the invention which comprise the additional elements and open patterns of adhesive delineated hereinabove.

Referring again to FIG. 1, an exemplary disposable diaper of this configuration comprises the following. The topsheet is a nonwoven hydrophobic polypropylene having a basis weight of from about fifteen (15) to about thirty (30) grams per square meter. The top and back wet-strength tissues 22 and 26, respectively, are portions of a sheet of wet-strength tissue which is wrapped about the core 23 to form an envelope thereabout, and which tissue sheet has overlapped longitudinally extending edge portions disposed between the core and the backsheet; and the wet-strength tissue has a basis weight of from about sixteen (16) to about twenty-three (23) grams per square meter, and machine and cross-machine wet tensile strengths of from about one-hundred-fifty (150) to about four-hundred (400) grams per sample having a width of about two-and-fifty-four-hundredths (2.54) centimeters, and from about seventy-five (75) to about one-hundred-twenty-five (125) grams per sample having a width of about two-and-fifty-four-hundredths (2.54) centimeters, respectively. Such tissue paper is excellent for obviating sifting out of the fibers of the absorbent core and, in embodiments comprising supersorber particulate, for also obviating sifting out of such particulate matters. The core 23 is an airlaid matt of cellulosic fibers which are substantially unbonded to each other through the thickness of the core, and the matt has a basis weight of from about three-hundred-ten (310) grams per square meter to about twelve-hundred-forty (1240) grams per square meter; and density of about seven-hundredths (0.07) grams per cubic centimeter in its crotch region and about three-hundredths (0.03) grams per cubic centimeter in its end regions. The backsheet 27 is matte-finish polyethylene having a nominal thickness of about one mil (about 0.0254 mm). The adhesive used for glue beads 46 and 60 is hot melt adhesive; and the adhesive used for adhesive networks 49 and 52 is also preferably hot melt adhesive of the pressure sensitive type. It is, however, not intended to limit the present invention to these materials or weights or the like inasmuch as such parameters may be changed to provide embodiments of the invention in a variety of sizes, and capacities, and the like.

A preferred pressure sensitive hot melt adhesive for constituting adhesive networks 49 and 52, FIG. 1, is identified by Adhesive Specification No. 990-374 of Findley Adhesives Inc. and a preferred non-pressure sensitive hot melt adhesive for constituting adhesive networks 49 and 52 is Stock No. 34-2857 which is available from National Starch Company.

Core slumping as used hereinbefore is, briefly, determined by drawing horizontal lines on the leading and trailing edges of the core of a disposable diaper. The flat diaper is submerged in water for two (2) minutes, U-folded in half, removed from the water, and allowed to hang from its waistband edges in the U-folded configuration for twenty-four to forty-eight hours. The slumping distance between the original horizontal lines and the receded edges of the core are then measured.

Core roping as used hereinbefore is determined by securing a disposable diaper on an articulated dummy which has a walking motion. The articulated dummy is caused to have a walking type motion for five (5) minutes. The diaper is then removed from the apparatus, and the core is measured for width reduction, tears and hard spots. The width reduction of the core is its degree of roping.

Demand wetability as used hereinbefore is, briefly, a term which comprises absorbent capacity and wetting rate. Essentially, wetting rate is measured in terms of volume thereby giving partial capacity as a function of time, and thereby ultimately giving the total capacity.

Referring now to the absorbent particulate matter which has been referred to hereinbefore as supersorbers, hydrogel materials are very effective. By "hydrogel" as used herein is meant an inorganic or organic compound capable of absorbing aqueous fluids and retaining them under moderate pressures. For good results, the hydrogels should be water insoluble. Examples are inorganic materials such as silica gels and organic compounds such as cross-linked polymers. Cross-linking may be by covalent, ionic, vander Waals, or hydrogen bonding. Examples of polymers include polyacrylamides, polyvinyl alcohol, ethylene maleic anhydride copolymers, polyvinyl ethers, hydroxypropyl cellulose, carboxymethyl cellulose, polyvinly morpholinone, polymers and copolymers of vinyl sulfonic acid, polyacrylates, polyacrylamides, polyvinyl pyridine and the like. Other suitable hydrogels are those disclosed in U.S. Pat. No. 3,901,236, issued to Assarsson et al., Aug. 26, 1975, the disclosures of which are incorporated herein by reference. Particularly preferred polymers for use herein are hydrolyzed acrylonitrile grafted starch, acrylic acid grafted starch, polyacrylates, and isobutylene maleic anhydride copolymers, or mixtures thereof.

For the purpose of utilizing hydrogels in the present invention, it is essential that relatively dry hydrogel particles be used. Also, neither the fibers, the particles nor the mixture of fibers and particles should be exposed to water in its liquid form, or another solvent, at any time during this process or subsequent thereto. When wet hydrogel particles are used, the fibers tend to become entangled and/or bonded with the particles which result in undesirable stiffness of the absorbent structure. Additionally, wet hydrogel particles would obviously have less absorbency efficacy in the product inasmuch as their potential absorbency would already be diminished.

As used herein, "dry" does not mean "absolutely water-free". For example, under normal storage and handling conditions, hydrogel particles take up some moisture. The hydrophilic fibers also take up some moisture during storage. Furthermore, it may be desirable to use humidified air for air transport of the fibers and the hydrogel particles, to avoid dusting. Under such process conditions, the hydrogel particles and the fibers will take up even more moisture, but such should be limited so that it does not unduly affect the practice of the present invention.

Additional alternate embodiments may comprise more or less elements as described above: particularly under DISCLOSURE OF THE INVENTION. For example and not by way of limitation such alternate embodiments may omit the top wet-strength tissue 22 in which case the topsheet is the liquid permeable lamina referred to in the appended claims: otherwise, of course, the "liquid permeable lamina" of the claims is an internal lamina and is preferably wet-strength tissue as described above. Additionally or alternatively the various laminae of other alternate embodiments may be secured together by additional open patterns of networks of filaments of adhesive or hosts of globulettes of adhesive as described above, rather than by the arrays of glue beads 46 and 60. Such open patterns of adhesive obviate the stress concentrations and stiffness precipitated by such glue beads.

While particular and alternate embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A disposable waste-containment garment comprising an absorbent core, a liquid permeable lamina, and a liquid impermeable backsheet, said absorbent core comprising a mass of fibers substantially devoid of interfiber bonds, said absorbent core being disposed intermediate said lamina and said backsheet, and adhesively secured in face to face relation to said lamina with an open pattern of adhesive having an average weight of from about eight-tenths to about four-and-seven-tenths grams per square meter.

2. The disposable waste-containment garment of claim 1 wherein said open pattern of adhesives comprises a reticulated network of filaments of adhesive.

3. The disposable waste-containment garment of claim 1 wherein said open pattern of adhesives comprises a host of globulettes of adhesive.

4. The disposable waste-containment garment of claim 2 or 3 wherein said filaments or globulettes of adhesive have effective diameters about equal in order of magnitude as the effective average diameter of the fibers which constitute said absorbent core.

5. The disposable waste-containment garment of claim 1 wherein said open pattern of adhesive weights from about two to about three-and-six-tenths grams per square meter.

6. The disposable waste-containment garment of claim 1 wherein said open pattern of adhesive weights about three-and-one-tenth grams per square meter.

7. The disposable waste-containment garment of claim 1 wherein said adhesive is a hot melt adhesive.

8. The disposable waste-containment garment of claim 1 or 7 wherein said adhesive is a pressure sensitive adhesive.

9. The disposable waste-containment garment of claim 1 further comprising an envelope having at least one liquid pervious wall, and said absorbent core further comprises a quantity of elements of highly liquid absorbent matter, said core being sealed within said envelope, and said lamina being a said wall of said envelope.

10. The disposable waste-containment garment of claim 9 wherein the weight of said quantity of said highly liquid absorbent matter is in the range of from about ten to about twenty-five percent by weight of said absorbent core.

11. The disposable waste-containment garment of claim 1 wherein the outwardly facing surface of said lamina is the surface of said garment intended for contact with the skin of a wearer of said garment and is denominated the topsheet of said garment.

12. The disposable waste-containment garment of claim 1 wherein said garment further comprises a liquid permeable topsheet, and said lamina being disposed intermediate said topsheet and said absorbent core.

13. The disposable waste-containment garment of claim 12 wherein said lamina and said topsheet are secured together in face to face relation with an other open pattern of adhesive.

14. The disposable waste-containment garment of claim 13 wherein said other open pattern of adhesive has a weight of from about eight-tenths to about four-and-seven-tenths grams per square meter.

15. The disposable waste-containment garment of claim 1, 9, 12 or 13 further comprising an additional open pattern of adhesive which is disposed to adhesively secure said absorbent core to said backsheet, said additional open pattern being a reticulated network of filaments of adhesive.

16. The disposable waste-containment garment of claim 1, 9, 12 or 13 further comprising another liquid permeable lamina which is disposed intermediate said absorbent core and said backsheet, and which said other liquid permeable lamina is adhesively secured in face to face relation with said absorbent core with a first additional open pattern of adhesive.

17. The disposable waste-containment garment of claim 16 wherein said other liquid permeable lamina is also adhesively secured to said backsheet with a second additional open pattern of adhesive.

18. The disposable waste-containment garment of claim 17 wherein said first and second additional open patterns of adhesive are reticulated networks of filaments of adhesives.

19. The disposable waste-containment garment of claim 18 wherein said adhesives are hot melt, pressure sensitive adhesives.

20. The disposable waste-containment garment of claim 16 wherein said first additional open pattern of adhesive is a reticulated network of filaments of adhesive.

21. The disposable waste-containment garment of claim 20 wherein said adhesive is a hot melt, pressure sensitive adhesive.

22. The disposable waste-containment garment of claim 9, 12, 13 or 14 wherein said adhesives are hot melt, pressure sensitive adhesives.

23. The disposable waste-containment garment of claim 9, 12, 13 or 14 wherein both of said open patterns of adhesive are reticulated networks of filaments of adhesives.

24. The disposable waste-containment garment of claim 23 wherein said adhesives are hot melt, pressure sensitive adhesives.

25. The disposable waste-containment garment of claim 24 wherein said filaments of adhesive have effective diameters about equal in order of magnitude as the effective average diameter of the fibers which constitute said absorbent core.

26. A disposable waste-containment garment comprising an absorbent core, a liquid permeable lamina, and a liquid impermeable backsheet, said absorbent core comprising a mass of fibers substantially devoid of inter-fiber bonds, said absorbent core being disposed intermediate said lamina and said backsheet, and adhesively secured in face to face relation to said lamina with a reticulated network of filaments of hot melt adhesive.

27. The disposable waste-containment garment of claim 26 wherein the outwardly facing surface of said lamina is the surface of said garment intended for contact with the skin of a wearer or said garment and is denominated the topsheet of said garment.

28. The disposable waste-containment garment of claim 27 wherein said garment further comprises a liquid permeable topsheet, and said lamina being disposed intermediate said topsheet and said absorbent core.

29. The disposable waste-containment garment of claim 28 wherein said lamina and said topsheet are secured together in face to face relation with another open pattern of adhesive.

30. A disposable waste-containment garment comprising an absorbent core, a liquid permeable lamina, and a liquid impermeable backsheet, said absorbent core comprising a mass of fibers substantially devoid of inter-fiber bonds, said absorbent core being disposed intermediate said lamina and said backsheet, and adhesively secured in face to face relation to said lamina with an open pattern of adhesive, said garment further comprising a liquid permeable topsheet, and said lamina being disposed intermediate said topsheet and said absorbent core.

31. The disposable waste-containment garment of claim 30 wherein said lamina and said topsheet are secured together in face to face relation with another open pattern of adhesive.

32. The disposable waste-containment garment of claim 12, 26 or 30 wherein the edges of said liquid permeable lamina are also adhesively secured to said backsheet with said absorbent core sealed therebetween, said absorbent core further comprising a quantity of elements of highly liquid absorbent matter, said quantity of said highly liquid absorbent matter being in the range of from about ten to about twenty-five percent by weight of said absorbent core.

* * * * *